United States Patent
Slade, Jr. et al.

(10) Patent No.: US 11,008,264 B2
(45) Date of Patent: May 18, 2021

(54) METHODS AND SYSTEMS FOR MEASURING PLASMA RENIN ACTIVITY

(71) Applicant: Laboratory Corporation of America Holdings, Burlington, NC (US)

(72) Inventors: William O. Slade, Jr., Durham, NC (US); Russell Philip Grant, Chapel Hill, NC (US); Christopher Michael Shuford, Mebane, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 564 days.

(21) Appl. No.: 15/815,754

(22) Filed: Nov. 17, 2017

(65) Prior Publication Data

US 2018/0134634 A1    May 17, 2018

Related U.S. Application Data

(60) Provisional application No. 62/423,550, filed on Nov. 17, 2016.

(51) Int. Cl.
| | | |
|---|---|---|
| *G01N 33/68* | (2006.01) | |
| *C07B 59/00* | (2006.01) | |
| *C07K 7/06* | (2006.01) | |
| *C12Q 1/37* | (2006.01) | |

(52) U.S. Cl.
CPC ............. *C07B 59/008* (2013.01); *C07K 7/06* (2013.01); *C12Q 1/37* (2013.01); *C12Y 304/21004* (2013.01); *G01N 33/68* (2013.01); *G01N 33/6842* (2013.01); *G01N 33/6848* (2013.01); *C12Q 2545/114* (2013.01); *G01N 2333/4703* (2013.01); *G01N 2333/575* (2013.01)

(58) Field of Classification Search
CPC .. C07B 59/008; G01N 33/68; G01N 33/6848; G01N 2333/575; G01N 2333/4703; C07K 7/06; C12Q 1/37; C12Q 2545/114; C12Y 304/21004
See application file for complete search history.

(56) References Cited

U.S. PATENT DOCUMENTS

| | | | |
|---|---|---|---|
| 3,984,532 A | 10/1976 | Fernandez De Castro | |
| 5,869,832 A | 2/1999 | Wang et al. | |
| 7,834,313 B2 | 11/2010 | Bystrom et al. | |
| 7,846,748 B2 | 12/2010 | Borchers | |
| 8,106,351 B2 | 1/2012 | Bystrom et al. | |
| 8,362,417 B2 | 1/2013 | Bystrom et al. | |
| 2010/0219338 A1 | 9/2010 | Bystrom et al. | |
| 2018/0231563 A1* | 8/2018 | Shimada | G01N 33/68 |

OTHER PUBLICATIONS

Davidson, Association of Clinical Biochemists, 2002, 39: 273-280. (Year: 2002).*

(Continued)

*Primary Examiner* — Allison M Fox
*Assistant Examiner* — Qing Xu
(74) *Attorney, Agent, or Firm* — Kilpatrick Townsend & Stockton LLP

(57) ABSTRACT

Disclosed are methods and systems for the quantification of AngI and/or determination of plasma renin activity in a sample. The methods and systems disclosed herein can be useful for diagnosis of hypertension, aldosteronism and other abnormalities of the renin angiotensin aldosterone system (RAAS).

35 Claims, 2 Drawing Sheets

Specification includes a Sequence Listing.

(56) References Cited

OTHER PUBLICATIONS

Wright et al., Brain Research Reviews, 1997, 25:96-124 (Year: 1997).*
Hildebrand, D. et al., "Proteolytic Processing of Angiotensin-I in Human Blood Plasma," PLoS One 8(5):364027 (2013) 12 pgs.
Lee, Jenny et al., "Gold Ion-Angiontensin Peptide Interaction by Mass Spectrometry," J. Am. Soc. Mass Spectrom. 23:942-951 (2012).
Lee, Jenny et al., "Supplementary Material—Gold Ion-Angiontensin Peptide Interaction by Mass Spectrometry," pp. 1-27, May 1, 2012.
Reid, J. et al., "Towards the Development of an Immuno MALDI (iMALDI) Mass Spectrometry Assay for the Diagnosis of Hypertension," J. Am. Soc. Mass. Spectrom. 21:1680-1686 (2010).
Wilbur, W.J. and Lipman, D.J., "Rapid similarity searches of nucleic acid and protein data banks," Proc. Natl. Acad. Sci. USA 80(3):726-730 (1983).
Van Der Gugten, G. and Holmes, D., "Quantitation of Plasma Renin Activity in Plasma Using Liquid Chromatography—Tandem Mass Spectrometry (LC-MS/MS)," Clinical Applications of Mass Spectrometry in Biomolecular Analysis 1378:243-253 (2016).
International Patent Application No. PCT/US2017/062126, International Search Report and Written Opinion dated Feb. 13, 2018.
Bystrom, C. et al., "Plasma Renin Activity by LC-MS/MS: Development of a Prototypical Clinical Assay Reveals a Subpopulation of Human Plasma Samples with Substantial Peptidase Activity," Clin. Chem. 56(10):1561-1569 (2010).
Cawood, M. "Measurement of Plasma Renin Activity," Methods in Mol. Biol. 324:187-196 (2006).
Fredline, V. et al., "Measurement of Plasma Renin Activity with Use of HPLC-Electrospray-Tandem Mass Spectrometry," Clin. Chem. 45(5):659-664 (1999).
Sullards, M. and Reiter, J., "Primary and Secondary Locations of Charge Sites in Angiotensin II $(M+2H)^{2+}$ Ions Formed by Electrospray Ionization," J. Am. Soc. Mass Spectrom. 11:40-53 (2000).
Van Der Gugten, J. et al., "Supported liquid extraction offers improved sample preparation for aldosterone analysis by liquid chromatography tandem mass spectrometry," J. Clin. Pathol. 65:1045-1048 (2012).
Xiao, X. et al., "Determination of angiotensin converting enzyme inhibitory activity by high-performance liquid chromatography/ electrospray-mass spectrometry," J. Chromatography B 834:48-54 (2006).
Yi, J. et al., "Intrinsic Peptidase Activity Causes a Sequential Multi-Step Reaction (SMSR) in Digestion of Human Plasma Peptides," J. Proteome Res. 7:5112-5118 (2008).
EP Application No. 17823249.2 , Office Action, dated Jun. 9, 2020, 10 pages.
CA 3,041,724, Office Action, Jan. 4, 2021, 5 pages.

\* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Asp Arg Val Tyr Ile His Pro Phe His Leu
1               5                   10

<210> SEQ ID NO 2
<211> LENGTH: 8
<212> TYPE: PRT
<213> ORGANISM: Artificial Sequence
```

```
<220> FEATURE:
<223> OTHER INFORMATION: Synthetic construct

<400> SEQUENCE: 2

Val Tyr Ile His Pro Phe His Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: labeled with a heavy isotope
<220> FEATURE:
<221> NAME/KEY: MISC_FEATURE
<222> LOCATION: (7)..(7)
<223> OTHER INFORMATION: labeled with a heavy isotope
<220> FEATURE:
<221> NAME/KEY: MISC_FEATURE
<222> LOCATION: (8)..(8)
<223> OTHER INFORMATION: labeled with a heavy isotope

<400> SEQUENCE: 3

Asp Arg Val Tyr Ile His Pro Phe His Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: labeled with a heavy isotope
<220> FEATURE:
<221> NAME/KEY: MISC_FEATURE
<222> LOCATION: (5)..(5)
<223> OTHER INFORMATION: labeled with a heavy isotope
<220> FEATURE:
<221> NAME/KEY: MISC_FEATURE
<222> LOCATION: (6)..(6)
<223> OTHER INFORMATION: labeled with a heavy isotope

<400> SEQUENCE: 4

Val Tyr Ile His Pro Phe His Leu
1               5
```

METHODS AND SYSTEMS FOR MEASURING PLASMA RENIN ACTIVITY

CROSS REFERENCE TO RELATED APPLICATION

This application claims the benefit of U.S. Provisional Application No. 62/423,550, filed Nov. 17, 2016, which is incorporated by reference in its entirety herein.

FIELD OF THE INVENTION

The present invention relates to methods and systems for determining the activity of plasma renin.

BACKGROUND

Plasma Renin Activity (PRA) measures the capacity of peripheral blood to generate the peptide angiotensin I (AngI) and is critical in the diagnosis of disorders of the renin angiotensin aldosterone system (RAAS). In the RAAS, angiotensinogen, constitutively manufactured by the liver, is hydrolyzed by renin, an enzyme manufactured by the renal juxtaglomerular apparatus, to form AngI. AngI can then be cleaved by angiotensin converting enzyme (ACE) to yield Angiotensin II (AngII), a potent vasoconstrictor and mediator of a number of downstream RAAS effects. Measurement of renin activity is useful in the differential diagnosis of individuals with hypertension. Renin levels will be elevated in patients with hypertension due to renal artery stenosis (i.e., renovascular hypertension). Measurement of renin activity can also be useful in the diagnosis of primary aldosteronism. Patients with secondary aldosteronism tend to have low renin levels. Renin activity can also be used to assess the adequacy of steroid substitution in patients with adrenal insufficiency. Renin activity will be normal in patients with adequate supplementation and will be elevated when steroid substitution is inadequate.

Thus, there is a need for improved lab tests to measure plasma renin activity. There is a need for improved lab tests that are more cost-efficient, thereby allowing more frequent testing and also provide clinicians testing results sooner.

SUMMARY

The present invention provides methods and systems for determining activity of plasma renin to generate angiotensin I (AngI), which is critical in the diagnosis of disorders of the renin angiotensin aldosterone system. In certain embodiments, the invention comprises a method to measure AngI generation by mass spectrometry and/or liquid chromatography—tandem mass spectrometry (LC-MS/MS). In certain embodiments, the invention comprises a method to confirm the correct specimen type is EDTA-Plasma. The invention may be embodied in a variety of ways.

In one embodiment the invention comprises a method for determining the amount of AngI in a sample. The method may comprise the steps of incubating the sample under conditions suitable to allow plasma renin to generate AngI peptide having the sequence NH2-DRVYIHPFHL-COOH (SEQ ID NO: 1) from angiotensinogen present in the sample; adding a protease or chemical hydrolyzing agent; incubating the sample under conditions to allow the protease or chemical hydrolyzing agent to hydrolyze the AngI to generate a defined AngI cleavage product; ionizing the AngI cleavage product to produce one or more ions detectable by mass spectrometry; and detecting the AngI cleavage product ions by mass spectrometry.

In certain embodiments, the method may include the use of an internal standard. For example, the method may comprise the step of adding a stable isotope-labeled AngI peptide (SIL-AngI) to the sample as an internal standard. As discussed in detail below, the internal standard may be selected from a variety of appropriate standards. In some embodiments, the SIL-AngI is a peptide NH2-DRV^YIHP^F^HL-COOH (SEQ ID NO: 3) wherein ^ indicates an amino acid labeled with a heavy isotope. For example, in one embodiment, V^ is (13C)5H11(15N)O2, having a mass shift of +6; P^ is (13C)5H9(15N)O2, having a mass shift of +6; and F^ is (13C)9H11(15N)O2, having a mass shift of +6. It is noted that there are other embodiments, wherein the SIL-AngI is a peptide NH2-DRVYIHPFHL-COOH (SEQ ID NO: 1) wherein many combinations of amino acids could be labeled with a heavy isotope, not confined to the internal standard used in example studies herein (SEQ ID NO: 3).

The internal standard provides a way to quantify the amount of the AngI peptide and/or AngI cleavage product at each step. In alternate embodiments, the SIL-AngI peptide is added before or after plasma renin mediated generation of AngI, but prior to the step of adding a protease. Thus, in certain embodiments, the amount of AngI cleavage product is directly proportional to the amount of an SIL-AngI cleavage product generated by the protease.

The method may also comprise external calibration (i.e., reference) standards which provide a known amount of AngI for comparison to the sample so as to quantify the sample AngI. Thus, in certain embodiments, the method may comprise the step(s) of generating a plurality of calibration standards comprising known amounts of AngI in a suitable matrix, wherein the reference standards are AngI of SEQ ID NO: 1 that goes through the same steps as the sample AngI. In certain embodiments, the external calibration standard do not go through all of the assay steps, but are added at the final steps of ionization and mass spectrometry. Thus, in certain embodiments, the amount of AngI in the sample is quantified by comparing the amount of AngI in the sample to the amount of AngI in at least one of the plurality of calibration standards. The calibration standards generally should include a concentration range that spans the expected range of AngI in the samples. For example, in certain embodiments, the calibration standards comprise AngI ranging from 0.25 to 100 ng/mL. Or larger or more narrow ranges may be used.

The method comprises generating an AngI derivative for MS/MS measurement. In certain embodiments, the derivative is generated by incubating the sample AngI with a protease. In certain embodiments, the protease is a serine protease. For example, in one embodiment, the protease is trypsin. For example, in certain embodiments, protease cleavage generates an AngI cleavage product having the sequence NH2-VYIHPFHL-COOH (SEQ ID NO: 2). In in certain embodiments, the protease generates a SIL-AngI cleavage product having the sequence NH2-V^YIHP^F^HL-COOH (SEQ ID NO: 4).

In certain embodiments, the AngI derivative (i.e., cleavage product) is generated by hydrolysis. For example, in certain embodiments, the chemical hydrolysis agent is formic acid, acetic acid, hydrochloric acid, or any other agent capable of hydrolyzing AngI.

Where the AngI cleavage product is AngI of SEQ ID NO: 2, the AngI ions are selected from the group consisting of ions having a mass/charge ratio of 513.3±2, 269.2±2, 392.7±2, 257.1±2. Similarly, where the SIL-AngI cleavage product is SIL-AngI of SEQ ID NO: 4, the SIL-AngI ions are selected from the group consisting of ions having a mass/charge ratio of 524.3±2, 779.5±269.2±2.

Other steps may be included in the method. For example, the method may, in certain embodiments, comprise the step of terminating plasma renin activity prior to the step of protease digestion. As discussed in more detail below, a variety of chemical agents and or physical treatments (e.g., heat) may be used to terminate plasma renin activity. For example, in certain embodiments, methanol is added to the sample to terminate plasma renin activity. Where an organic solvent (e.g., methanol) is added, the method may further comprise the step of evaporating the solvent (e.g., methanol) and then reconstituting the sample in a buffer prior to the step of protease digestion.

The AngI cleavage product (and internal standard) in the sample, and optionally, also the calibration standards, may be further purified prior to mass spectrometry. For example, in certain embodiments, the method comprises the step of subjecting the AngI cleavage product to liquid chromatography prior to mass spectrometry.

As discussed in detail herein, a variety of mass spectrometry methods may be used. In one embodiment, the ionization is positive electrospray ionization with selected reaction monitoring (SRM).

A variety of samples may be used. In certain embodiments, the sample is a biological fluid obtained from a patient. For example, in certain embodiments, the biological fluid is plasma. In an embodiment, the plasma comprises ethylenediaminetetraacetic acid (EDTA) as an anticoagulant.

In certain embodiments, the samples are verified as being plasma samples that contain EDTA. Thus, the method may include removing an aliquot from the sample and testing for the presence of EDTA prior to the incubation step to generate AngI. In one embodiment, the test for the presence of EDTA comprises addition of a colorimetric agent, o-cresolphthalein complexone, to react with calcium ions in the sample, such that samples comprising EDTA remain substantially unchanged in color, whereas samples that do not have EDTA turn color due to reaction of calcium with the colorimetric agent.

The method is additionally a method of measuring plasma renin activity (PRA) according to any of the preceding embodiments, wherein the level of PRA is calculated based on the amount of AngI peptide in the sample. In an embodiment, the plasma renin activity is defined by the amount of AngI generated per unit time. For example, in certain embodiments, the plasma renin activity is expressed as ng/mL/hr. In one embodiment, the plasma renin activity has an analytically measurable range (AMR) ranging from about 0.167-66.667 ng/mL/hr.

Embodiments of the assay are both sensitive and highly specific. In certain embodiments, the lower limit of quantification (LLOQ) is 0.167 ng/mL/hr and the upper limit of quantification (ULOQ) is 66.667 ng/mL/hr.

In other embodiments, the invention comprises a system for determining the level of AngI and/or the activity of plasma renin in a sample. The system may comprise various stations and/or components for performing steps of the method disclosed herein. For example, the system may comprise a station (or component) for incubating the sample under conditions to generate AngI from angiotensinogen. The system may also optionally comprise a station (or component) for adding an internal standard (e.g., SIL-AngI) to the AngI peptide. In addition, the system may also optionally comprise a station (or component) for termination of plasma renin mediated generation of AngI. The system may also comprise a station (or component) for digesting (or hydrolyzing) the AngI and the optionally added SIL-AngI to generate cleavage products of each of the AngI and the optional SIL-AngI. In certain embodiments, the components for incubating the sample, adding the internal standard, terminating plasma renin activity and/or performing the protease digestion (and/or hydrolysis) may be performed as part of the same station.

The system may also comprise a station for mass spectrometry. Thus the system may comprise a station for ionizing the AngI and the optional SIL-AngI enzymatic cleavage products to generate a multiply charged gas-phase ions of the AngI cleavage product and the optional SIL-AngI cleavage product. Optionally, the system may also comprise a station for analyzing the multiply charged gas phase ion by mass spectrometry to determine the presence and/or amount of the AngI cleavage product and the optional SIL-AngI cleavage product in the sample, wherein the amount of the cleavage products is indicative of the activity of plasma renin in the sample. The system may also comprise a station for chromatographically separating the cleavage product using liquid chromatography (e.g., HPLC) prior to mass spectrometry.

As noted above, the method may comprise the step of validating that the samples are plasma containing sufficient coagulant. Thus, in certain embodiments, the system may comprise a station for testing the sample for the presence of EDTA.

These and other embodiments are described herein.

BRIEF DESCRIPTION OF THE FIGURES

The invention may be better understood by reference to the following non-limiting figures.

DETAILED DESCRIPTION

Figure 1:
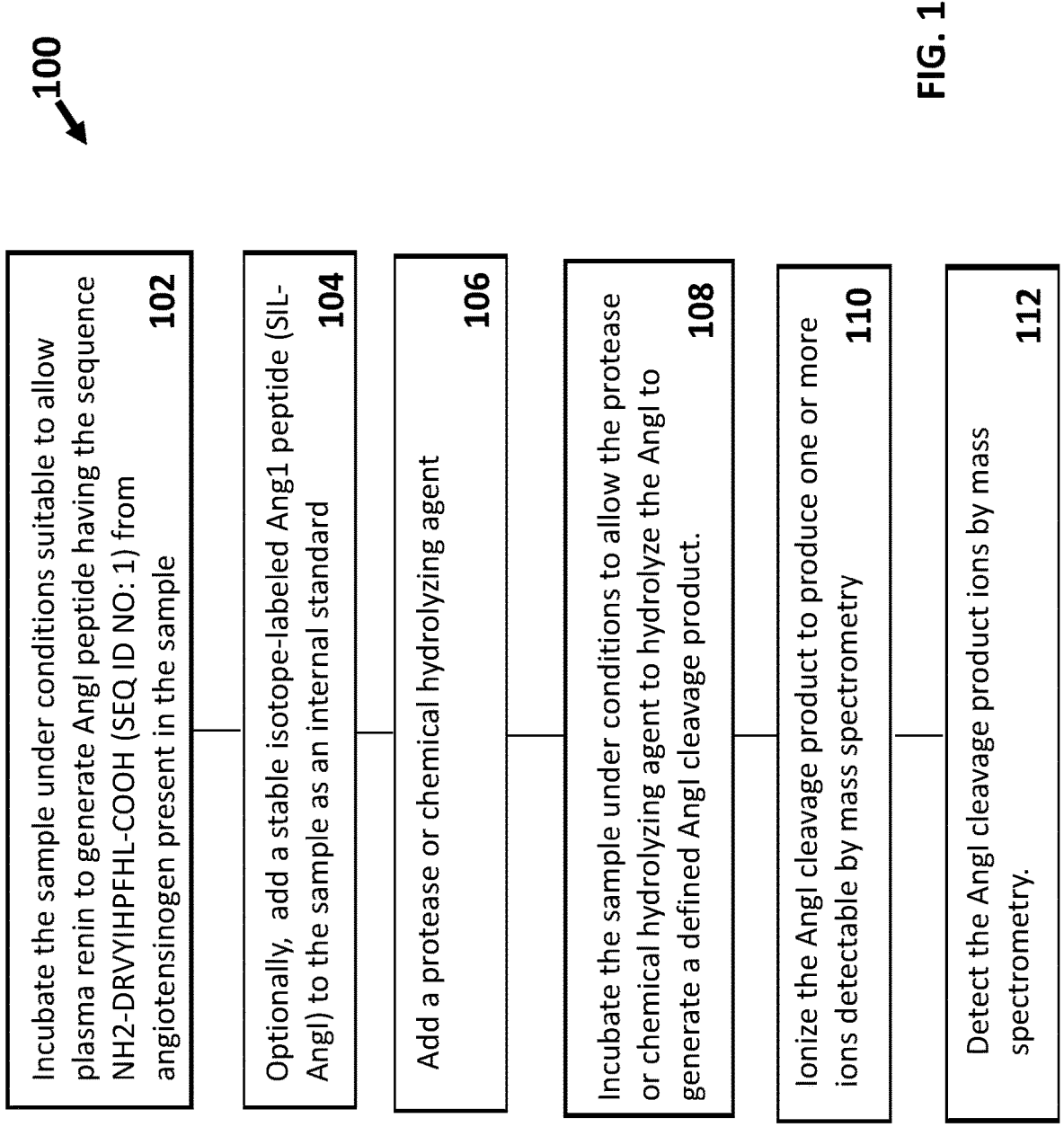
FIG. 1 is a flow chart of an embodiment of a method of the invention.

The following description recites various aspects and embodiments of the present invention. No particular embodiment is intended to define the scope of the invention. Rather, the embodiments merely provide non-limiting examples of various methods and systems that are at least included within the scope of the invention. The description is to be read from the perspective of one of ordinary skill in the art; therefore, information well known to the skilled artisan is not necessarily included.

ABBREVIATIONS

Various abbreviations may be used in the application. In most, if not all, instances, the meanings of such abbreviations are known to those of skill in the art. These abbreviations include the following abbreviations, whose meanings are provided. Other abbreviations are defined herein.
AMR: Analytically Measurable Range
AngI: Angiotensin 1
APCI: atmospheric pressure chemical ionization
ARR: Aldosterone-Renin-Ratio
BSA: bovine serum albumin
CE: capillary electrophoresis CRR: Clinically Reportable Range
CZE: capillary zone electrophoresis
DESI: desorption electrospray ionization
DMSO: dimethyl sulfoxide
EDTA: Ethylenediaminetetraacetic Acid
ESI: electrospray ionization
FAB: fast-atom bombardment
HPLC: high-performance liquid chromatography
LAESI: laser ablation electrospray ionization
LC: liquid chromatography
LC-MS/MS: liquid chromatography—tandem mass spectrometry
LLOQ: lower limit of quantitation
LSI: laser spray ionization
MALDESI: matrix-assisted laser desorption electrospray ionization
MALDI: matrix-assisted laser desorption ionization
MRM: multiple-reaction monitoring
MS: mass spectrometry
MS/MS: tandem mass spectrometry
m/z: mass to charge
PMSF: phenylmethane sulfonyl fluoride
PRA: Plasma Renin Activity
PRM: parallel-reaction monitoring
QCs: quality controls
Q-TOF: quadrupole time-of-flight
RAAS: Renin Angiotensin Aldosterone System
RIA: radioimmunoassay
SIM: selected ion monitoring
SPH: St. Paul's Hospital
SRM: selected reaction monitoring
Tris: tris(hydroxymethyl)aminomethane
ULOQ: upper limit of quantitation Definitions The following terms, unless otherwise indicated, shall be understood to have the following meanings:

As used herein, the terms "a," "an," and "the" can refer to one or more unless specifically noted otherwise.

Throughout this application, the term "about" is used to indicate that a value includes the inherent variation of error for the device, the method being employed to determine the value, or the variation that exists among the study subjects.

As used herein, the terms "enzyme activity" or "enzymatic activity" refer to a measure of plasma renin specific activity as compared to a reference standard or a calibration curve of a reference standard. In some cases, plasma renin activity is compared to a population of normal individuals called a reference interval. This reference would include lower and upper 95% confidence interval limits for plasma renin activity in an ostensible healthy population. The terms can be used in conjunction with the term "amount" or "level."

As used herein, the terms "subject," "individual," and "patient" are used interchangeably. The use of these terms does not imply any kind of relationship to a medical professional, such as a physician.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationary phases and the mobile phase. LC includes, for example, reverse phase liquid chromatography (RPLC) and high pressure liquid chromatography (HPLC). In some cases, LC refers to reverse phase LC with a hydrophobic stationary phase in combination a mobile phase comprised of water and/or water-miscible organic solvents, such as methanol or acetonitrile. In some case, LC may refer to ion exchange chromatography, affinity chromatography, normal phase liquid chromatography, or hydrophilic interaction chromatography.

As used herein the term "capillary electrophoresis" (CE) refers to a process for the separation of one or more molecules or analytes in a sample from other analytes in the sample, based on their ionic mobility in an electrolyte solution while exposed to an electric field. CE includes, for example, capillary zone electrophoresis (CZE).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" refers to a technique for the identification and/or quantitation of molecules in a sample. MS includes ionizing the molecules in a sample to form charged molecules (ions) in the gas phase; separating the charged molecules according to their mass-to-charge ratio; and detecting the charged molecules. MS allows for both the qualitative and quantitative detection of molecules in a sample. The molecules may be ionized and detected by any suitable means known to one of skill in the art. The phrase "tandem mass spectrometry" or "MS/MS" is used herein to refer to a technique for the identification and/or quantitation of molecules in a sample, wherein multiple selective steps of mass spectrometry occur, either simultaneously using more than one mass analyzer or sequentially using a single mass analyzer. As used herein, a "mass spectrometer" is an apparatus that includes a means for ionizing molecules, selecting molecules and detecting charged molecules.

As used herein, "electrospray ionization" or "ESI" refers to a technique used in mass spectrometry to ionize molecules in a sample while avoiding fragmentation of the molecules. The sample is dispersed by the electrospray into a fine aerosol. The sample will typically be mixed with a solvent, usually a volatile organic compound (e.g., methanol or acetonitrile) mixed with water. The aerosol is then transferred to the mass spectrometer through an orifice, which can be heated to aid further solvent evaporation from the charged droplets and, ultimately, form gas-phase ions of the molecules in the sample.

As used herein, the term "stable isotopically-labeled" or "stable isotope-labeled" encompasses the process of enriching a molecule with a non-radioactive isotope of a given atom so as to alter the average mass of said atom within a molecule and thereby alter the average mass of said molecule. Generally, this is accomplished by replacing the light isotopes more frequently found in nature and in natural molecules (e.g., carbon-12 or nitrogen-14), with the less common heavy isotopes (e.g., carbon-13 or nitrogen-15).

As used herein, a "quadrupole analyzer" is a type of mass analyzer used in MS. It consists of four circular rods (two pairs) that are set highly parallel to each other. The quadrupole may be in triple quadrupole format as is known in the art. The quadrupole analyzer is the component of the instrument that can resolve the charged molecules of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer. For "selected reaction monitoring" or "SRM," the amplitude of the direct current and the radio frequency voltages are set to observe only specific masses The term "centrifugation" refers to a process that involves the application of the centripetal force for the sedimentation of heterogeneous mixtures with a centrifuge. This increases the effective gravitational force on a sample, for example, contained in a tube, to more rapidly and completely cause the precipitate (pellet) to gather on the bottom of the tube. The remaining solution is termed "supernatant."

The terms "substrate" or "enzyme substrate" are used herein to refer to a material on which an enzyme acts.

The term "exogenous" or "external" substrate is a substrate originating from outside the sample. In certain embodiments, the exogenous/external substrate is a "synthetic" substrate.

The term "synthetic" is used here to refer to a man-made molecule, for example, produced in a laboratory or other similar facility. This will encompass both chemical synthesis as well as recombinant molecular techniques (i.e., expression from a recombinant nucleic acid construct).

The term "sequence" can be used to refer to the order of amino acids in a polypeptide, which can also be described as "primary structure," or to a polypeptide molecule, such as a polypeptide with a particular order of amino acids.

As is known in the art, "proteins", "peptides," and "polypeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein. The term "peptide" is used to denote a less than full-length protein or a very short protein unless the context indicates otherwise.

The term "amino acid sequence" can be used to refer to the one letter amino acid code that defines a sequence of peptides. The amino acid notations used herein for the twenty genetically encoded L-amino acids are conventional and are as follows:

TABLE 1

| One Letter Abbreviation | Three Letter Abbreviation | Amino Acid |
|---|---|---|
| A | Ala | Alanine |
| N | Asn | Asparagine |

TABLE 1-continued

| One Letter Abbreviation | Three Letter Abbreviation | Amino Acid |
|---|---|---|
| R | Arg | Arginine |
| D | Asp | Aspartic acid |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

"Sequence identity" or "sequence similarity" in the context of two or more amino acid sequences, refer to two or more sequences or subsequences that are the same or have a specified percentage of amino acids that are the same (for example, 60%, 65%, 70%, 75%, 80%, 85%, 90%, 91%, 92%, 93%, 94%, 95%, 96%, 97%, 98%, 99%), or higher identity over a specified region, when compared and aligned for maximum correspondence over a comparison window or designated region. Various tools for measuring sequence similarity are available, such as protein BLAST available from National Center for Biotechnology Information, U.S. National Library of Medicine, Bethesda, Md., USA. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

As used herein, the term "similar" or "homologue" when referring to amino acid or nucleotide sequences means a polypeptide having a degree of homology or identity with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA*, 80:726-730). For example, homologous sequences may be taken to include amino acid sequences which in alternate embodiments are at least 70% identical, 75% identical, 80% identical, 85% identical, 90% identical, 95% identical, 96% identical, 97% identical, or 98% identical to each other.

As used herein, the term at least 90% identical thereto includes sequences that range from 90 to 99.99% identity to the indicated sequences and includes all ranges in between. Thus, the term at least 90% identical thereto includes sequences that are 91, 91.5, 92, 92.5, 93, 93.5. 94, 94.5, 95, 95.5, 96, 96.5, 97, 97.5, 98, 98.5, 99, 99.5 percent identical to the indicated sequence. Similarly the term "at least 70% identical includes sequences that range from 70 to 99.99% identical, with all ranges in between. The determination of percent identity is determined using the algorithms described herein.

The terms "cleavage," "enzyme cleavage" or "enzymatic cleavage" are used herein to refer to a process or a result of enzymatic hydrolysis of a polypeptide caused by an enzyme protease (peptidase or proteinase) or chemical hydrolysis to generate a defined product.

The term "cleavage site" is used herein to refer to a location of cleavage by a protease in a polypeptide. The term "cleavage site" encompasses and may be used to denote "specific cleavage site," meaning a cleavage site in a polypeptide for which a protease is specific.

The term "cleavage product" or "enzymatic cleavage product" is used herein to refer to a polypeptide resulting from enzymatic cleavage by a protease. For example, an AngI cleavage product can be a tryptic peptide generated from AngI as discussed herein.

Methods for Determining the Presence or Amount of Plasma Renin Activity

The invention may be embodied in a variety of ways. In certain embodiments, the invention comprises a method to measure AngI and/or plasma renin activity by mass spectrometry. In some embodiments tandem MS/MS is used. In some embodiments, plasma renin activity is measured by LC-MS/MS. Also included are systems for measuring plasma renin activity.

For example, and referring to FIG. 1, in one embodiment the invention comprises a method (100) for determining the amount of AngI in a sample. The method may comprise the step (102) of incubating the sample under conditions suitable to allow plasma renin to generate AngI peptide having the sequence NH2-DRVYIHPFHL-COOH (SEQ ID NO: 1) from angiotensinogen present in the sample. The method may also comprise the step (106) of adding a protease or chemical hydrolyzing agent. Also, the method may comprise the step (108) of incubating the sample under conditions to allow the protease or chemical hydrolyzing agent to hydrolyze the AngI to generate a defined AngI cleavage product. The method may also comprise the step (110) of ionizing the AngI cleavage product to produce one or more ions detectable by mass spectrometry. The method may further include the step (112) of detecting the AngI cleavage product ions by mass spectrometry. As discussed in more detail below, the method may additionally include the step (104) of adding a stable isotope-labeled AngI peptide (SIL-AngI) to the sample as an internal standard.

In some embodiments, the amount of plasma renin enzymatic activity in the sample need not be quantified. In some embodiments, the method can be used to determine the presence or absence of plasma renin enzymatic activity in a sample. In other embodiments, the method is used to determine the amount of AngI in a sample. For example, in some embodiments and/or aspects, the invention provides methods for determining an amount of AngI and/or plasma renin activity in a sample, comprising the steps of incubating the sample to generate AngI, optionally optimizing the sample chemistry to obviate protease activity from sample enzymes, optionally adding an internal standard (e.g., SIL-AngI), hydrolyzing the AngI and the optional internal standard, optionally terminating the hydrolysis in the sample being incubated, optionally chromatographically separating an AngI cleavage product and the internal standard cleavage product from other components of the sample using liquid chromatography, and ionizing the AngI cleavage product and the optional internal standard cleavage product to generate multiply charged ions that are analyzed by mass spectrometry to determine the amount of AngI cleavage product and the optional AngI internal standard cleavage product in the sample, wherein a ratio of the determined amounts of the AngI cleavage product and the AngI internal standard cleavage product is indicative of the amount of activity of plasma renin in the sample. Also, in certain embodiments, for example, where the sample is serum or plasma, an aliquot of the sample is tested to be sure that EDTA (an anticoagulant) is present in an amount sufficient to chelate certain divalent ions (e.g., Ca2+ and Mg2+).

The amount of activity in the sample may be determined by comparison to an external standard curve. For example, the quantity of AngI peptide may be compared to an external standard curve of calibration standards generated using a suitable matrix having known concentrations of AngI added. The method is not limited to a specific number of calibration levels. In some embodiments, only a single point is need to generate the calibration curve. In some embodiments, the calibrator may added into the sample.

An exemplary embodiment of the invention is a method for determining activity of plasma renin in a sample, which may include the steps of incubating the sample to generate AngI, NH2-DRVYIHPFHL-COOH (SEQ ID NO: 1) from angiotensinogen. Next, a synthetic stable isotope labeled AngI peptide analogue for AngI NH2-DRV^YIHP^F^HL-COOH (SEQ ID NO: 3) is optionally added. The use of a stable isotope labeled internal standard allows for correction due to less than 100% recovery of AngI peptide (or AngI cleavage product) at any step. In an embodiment, V^ is (13C)5H11(15N)O2, having a mass shift of +6; P^ is (13C)5H9(15N)O2, having a mass shift of +6; and F^ is (13C)9H11(15N)O2, having a mass shift of +6. The sample may then be subjected to optional termination of the reaction using methanol or another organic reagent, evaporation of the solvent and reconstitution of the AngI and the optional internal standard SIL-AngI in a buffer. At this point, a protease may be added to generate an AngI cleavage product peptide and a corresponding optional internal standard SIL-AngI cleavage product. In an embodiment, the protease is a serine protease. In an embodiment, the protease is trypsin. For example, in an embodiment, trypsin cleavage of AngI generates the peptide NH2-VYIHPFHL-COOH (SEQ ID NO: 2) and trypsin cleavage of the SIL-AngI generates NH2-V^YIHP^F^HL-COOH (SEQ ID NO: 4). Next, the method may include optionally, terminating the protease cleavage step. The method may further include optionally, chromatographically separating the AngI cleavage product and the optional SIL-AngI cleavage product from other components in the sample using liquid chromatography; and analyzing the AngI and SIL-AngI cleavage product(s) by mass spectrometry to determine presence or amount of cleavage product in the sample. The presence or the amount of the product of the AngI cleavage product in the sample is indicative of the presence or the amount of AngI in the sample. In an embodiment, the ratio of SIL-AngI cleavage product to measured AngI cleavage product is used to correct for loss of AngI at any step. In an embodiment, the method further comprises generating a plurality of calibration standards comprising known amounts of AngI in a suitable matrix. In an embodiment, the amount of AngI in the sample is quantified by comparing the amount of AngI in the sample to the amount of AngI in at least one of the plurality of calibration standards assayed as the hydrolyzed products.

In one embodiment, the internal standard is AngI labeled with heavy isotopes as described above. As is known, other types of internal standard may be employed. For example, the internal standard may be unlabeled but have a different amino acid sequence, or other amino acids in the peptide may be labeled. The internal standard, as well as the calibration standards may be made by chemical synthesis or recombinant methods. In some embodiments, the calibration standards may have the amino acid sequence shown in SEQ ID NO: 1 or SEQ ID NO: 2 and the SIL-AngI may have the have amino acid sequence shown in SEQ ID NO: 3. Additionally and/or alternatively, the internal standard may include additional sequences containing differently labeled amino acids. In alternate embodiments, the reference standards have at least 70%, 75%, 80%, 85%, 90%, 95% sequence similarity to SEQ ID NO: 1 or SEQ ID NO: 2, and the internal standard has at least 70%, 75%, 80%, 85%, 90%, 95% sequence similarity to SEQ ID NO: 3.

In an embodiment, plasma renin activity is proportional to the amount of AngI product created during the incubation period. The AngI product is proportional to the AngI derivative (e.g., a hydrolyzed cleavage product) that is measured by mass spectrometry. In certain embodiments, the serine protease incubation (to generate the AngI derivative) may be terminated by acid and/or temperature quenching of the enzyme. Also, in certain embodiments, the sample containing the AngI cleavage product and the optional SIL-AngI cleavage product may be analyzed directly using mass spectrometry. In certain embodiments, the AngI cleavage product and the optional SIL-AngI cleavage product is analyzed by liquid chromatography (LC) or another purification technique (e.g., capillary electrophoresis) coupled with tandem mass spectrometry (MS/MS) to measure the AngI product.

In an embodiment, the internal standard may be added before or after generation of AngI but prior to termination of the reaction with methanol or temperature. In an embodiment, the internal standard may be added after the addition of methanol, but prior to evaporation of the methanol and reconstitution of the sample in a buffer. In an embodiment, the measured analyte: internal standard ratio is proportional to the amount of AngI formed and, thereby, directly proportional to the plasma renin activity.

The ionization step results in the formation of multiply charged ions. In certain embodiments, the ionization step includes ionizing the AngI enzymatic cleavage product and the optional SIL-AngI cleavage product using an ionization technique, such as electrospray ionization, atmospheric pressure chemical ionization or atmospheric pressure photoionization.

The analyzing step allows for characterization and quantification of the multiply charged ions formed in the ionization step. In certain embodiments, the analyzing step includes determining the specific activity of plasma renin. In some embodiments, the analyzing step uses tandem mass spectrometry. Using the substrate of SEQ ID NO: 1 to generate the product of SEQ ID NO: 2, and the substrate of SEQ ID NO: 3 to generate the product of SEQ ID NO: 4, the analyzing step may, in certain embodiments, use ions having an m/z selected from the group consisting of 513.3±2, 269.2±2, 392.7±2, 257.1±2.

The methods according to the embodiments of the present invention may comprise providing a sample. In this context, the term "providing" is to be construed broadly. The term is not intended to refer exclusively to a subject who provided a biological sample. For example, a technician in an off-site clinical laboratory can be said to "provide" the sample, for example, as the sample is prepared for purification by extraction and/or chromatography.

The invention is not limited to any particular means of sample handling. In certain embodiments, the sample requires EDTA as an anticoagulant. For example, in certain embodiments, the sample is a plasma sample comprising EDTA. The amount of EDTA in the sample should be at a level that is sufficient to chelate the divalent ions (e.g., Ca2+, Mg2+) present in the sample. For example, in certain embodiments, the amount of EDTA added to the sample should result in an EDTA concentration of at least 0.5-3 mg/mL.

Thus, in certain embodiments, the method comprises the step of testing an aliquot of the sample for the presence of EDTA in the sample in an amount suitable to chelate the divalent ions present in the sample. The test for EDTA may be performed using a variety of methods. In some embodiments, the test for EDTA may comprise a colorimetric agent that detects the presence of divalent ions. A plasma sample that contains sufficient EDTA for chelation of divalent ions will not be able to interact with the colorimetric agent to produce a colorimetric signal. In an embodiment, the colorimetric agent is o-cresolphthalein complexone; this reagent reacts with calcium ions to produce a purple color. Thus, if EDTA is present in the sample in excess of the calcium ions, the sample will not change color upon addition of the colorimetric agent. If EDTA is not present in the sample, or is not present in an amount that chelates the free calcium ions, the sample will turn a purple color. Such samples are generally not suitable for the assay.

Termination of the plasma renin mediated generation of AngI, and/or the protease mediated digestion of AngI and the optional SIL-AngI in the sample being incubated is not limited to any particular method. In some embodiments, termination is accomplished by adding a precipitating reagent to the sample after the appropriate incubation period, in an amount sufficient to terminate the plasma renin enzymatic reaction. A precipitating reagent can be methanol, acetonitrile, acetone, 2-propanol, ammonium sulfate, trichloroacetic acid or perchloric acid. In some embodiments, temperature may be used to effectively terminate the reaction. The sample may be heated so as to inactivate the plasma renin or the sample may be cooled, potentially frozen, to slow the reaction to an effective stop. In some embodiments, the reaction may be stopped by adjusting the sample pH not conducive for plasma renin activity, for example, below about pH 3 or above about pH 9. In other embodiments, the reaction may be stopped by adding inhibitors of plasma renin (and/or the serine protease), such as Tekturna or other protease inhibitors. In some embodiments, it may not be necessary to terminate the enzymatic reaction. For example, plasma renin enzymatic reaction may be continuously monitored during the incubation step by repeated sampling over the course of time, rather than measurement at a single time point.

Partial purification of the sample may be used to provide a partially purified sample. Partial purification can be conducted at various stages of the method. For example, in some embodiments, partial purification can be conducted after incubation of the sample and termination of plasma renin activity, resulting in a sample comprising AngI. In some other embodiments, partial purification can be conducted prior to the incubation step. More than one partial purification step may be used in the methods according to the embodiments of the present invention. Partial purification is not limited by the method or the result of the partial purification. In some embodiments, the concentrations of one or more of the various components in the sample, other than the component of interest, have been reduced. For example, concentration of the other components may be reduced relative to the concentration of enzymatic cleavage product in the partially purified sample. In another example, concentration of the other components may be reduced relative to the concentration of AngI in the partially purified sample.

Thus, the term "removing" or "removal" does not necessarily imply the complete removal of a component. Some amount of the removed component can still be present in the partially purified sample, although its concentration relative to that of the component of interest will be lower than in the pre-extraction sample. In some embodiments, the relative concentration of the removed component to that of enzymatic cleavage product in the partially purified sample is no more than 90%, or no more than 75%, or no more than 50%, or no more than 33%, or no more than 25%, or no more than 10% or no more than 5%, or no more than 1%, of its relative concentration to enzymatic cleavage product in the sample prior to the partial purification step. The invention is not limited to any particular type of removed component. In some embodiments, one or more of the removed components is a compound that can interfere with the analysis by mass spectrometry or with liquid chromatography. One example of partial purification method is centrifugation after the termination of the reaction by addition of an organic solvent. During the centrifugation, the precipitated components of thus treated sample are removed, while the supernatant is further purified and/or analyzed.

In some embodiments of the invention, the partially purified sample can undergo one or more processing steps before chromatographic separation. For example, in some embodiments, the partially purified sample is evaporated. Then, the resulting residue is reconstituted in a solvent system. Any suitable solvent system can be used for reconstituting the residue. In some embodiments, the solvent system is a solvent system that is compatible with chromatographic separation. In some embodiments, the solvent system for reconstitution includes, but is not limited to, water, methanol, or mixtures thereof. In some other embodiments, the partially purified sample may undergo a chemical or enzymatic treatment so as to modify the enzymatic cleavage product. For example, the cleavage product may be chemically derivatized or further hydrolyzed. In some embodiments, the cleavage product may be further hydrolyzed with other enzymes.

In some embodiments, the methods include (comprise) a step of chromatographically separating the AngI and the optional SIL-AngI cleavage product(s) from other components in the sample, for example, using liquid chromatography. The invention is not limited to any particular manner of performing liquid chromatography. In general, the chromatographic separation step includes using at least one liquid chromatography (LC) column. In some embodiments, multiple LC columns are used, such as two or more, or three or more, or four or more LC columns. In some such embodiments two, three, four, five, six, eight or ten LC columns are used. In some such embodiments, two or more of these LC columns are arranged parallel to each other and are connected inline to the same mass spectrometer.

The invention is not limited to any particular types of columns. Any column suitable for the separation of enzymatic cleavage product can be used. In some embodiments, one or more analytical columns are used. In some embodiments, the column is a C18 column, but could be comprised of C12, C8, C4, Phenyl-hexyl, amide, amine, or PFP.

Further, the invention is not limited to any particular mobile phase. Any suitable mobile phase can be used, as long as the mobile phase is suitable for use with a particular LC column and for chromatographically separating enzymatic cleavage product in the LC column. In some embodiments, the mobile phase is comprised of acetonitrile (0-100%). Or, the mobile phase may be comprised of methanol (0-100%). In some such embodiments, the mobile phase employs a gradient, such that the relative ratios of two or more solvents are varied over time. In some embodiments, the mobile phase is comprised of ion pairing reagents, such as trifluoroacetic acid, formic acid, ammonium, heptafluorobutyric acid, and/or acetic acid.

In certain embodiments, two or more LC columns can be used in parallel and connected inline to the same mass spectrometer, e.g., to improve throughput. In some such embodiments, a sample (which can be a partially purified sample) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries, and the potential need to avoid interference with the analysis of the enzymatic cleavage product eluted from one or more of the other LC columns.

In some embodiments of the invention, an LC column can be placed in series with another column. For example, in some embodiments, suitable guard columns can be employed. Those of skill in the art are able to select appropriate guard columns for use in the present methods. In some embodiments, a guard column is placed in parallel with another LC column. Such series of two or more columns can also be arranged in parallel, such that there are two or more series of columns operating in parallel, where each series contains two or more columns. In other embodiments, online extraction columns may be employed. For example, online solid phase extraction columns may be used to separate the hydrolyzed AngI and optional SIL-AngI products in some embodiments of the method.

In some embodiments of the invention, the AngI and optional SIL-AngI enzymatic cleavage product may be purified by electrophoresis. For example, in some embodiments, the enzymatic cleavage product is separated from potentially interfering substances using capillary electrophoresis.

In some embodiments, the methods comprise analyzing the purified or separated enzymatic cleavage product by mass spectrometry to determine the presence or amount of the AngI and optional SIL-AngI enzymatic cleavage product. In some embodiments, two or more of the LC columns feed into the same mass spectrometer. In some further embodiments, three or more of the LC columns feed into the same mass spectrometer. In some embodiments, the mass spectrometer is part of a combined LC-MS system.

The invention is not limited to any particular type of mass spectrometer. Any suitable mass spectrometer can be used. In some embodiments, the method employs a tandem mass spectrometer. In some such embodiments, analyzing enzymatic cleavage product can include, ionizing enzymatic cleavage product, analyzing the ionized enzymatic cleavage product, fragmenting the enzymatic cleavage product ion into two or more fragment ions, and analyzing the fragment ions.

The invention is not limited to a mass spectrometer using any particular ionization methods. The method may utilize ionization techniques suitable to the generation of multiply charged ions from the enzymatic cleavage product. Suitable ionization methods include, but are not limited to photoionization, electrospray ionization, atmospheric pressure chemical ionization, and electron capture ionization. And in embodiments that employ fragmenting, any suitable fragmentation technique can be used. Suitable techniques include, but are not limited to collision induced dissociation, electron capture dissociation, electron transfer dissociation, infrared multiphoton dissociation, radiative dissociation, electron-detachment dissociation, and surface-induced dissociation.

In some embodiments, the tandem mass spectrometer is a Sciex API5500 triple quadrupole mass spectrometer. In some embodiments, the tandem mass spectrometer has an atmospheric pressure ionization source, and the analyzing step comprises an ionization method selected from the group consisting of photoionization, matrix assisted laser desorption/ionization (MALDI), electrospray ionization (ESI), atmospheric pressure chemical ionization (APCI), electron capture ionization, electron ionization, fast atom bombardment/liquid secondary ionization (FAB/LSI), field ionization, field desorption, thermospray/plasmaspray ionization, particle beam ionization, and so-called "hybrid ionization" techniques, such as laser ablation electrospray ionization (LAESI), desorption electrospray ionization (DESI) or matrix assisted laser desorption electrospray ionization (MALDESI). The ionization method may be in positive ion mode or negative ion mode. The analyzing step may also include multiple reaction monitoring (MRM, also referred to as selected reaction monitoring or SRM) or selected ion monitoring (SIM), and the two or more biomolecules are analyzed simultaneously or sequentially. In some embodiments, the analyzing step uses a quadrupole analyzer. In some embodiments, the mass spectrometer is a triple quadrupole mass spectrometer. In some embodiments, the analyzing step may be performed with product ion scanning on quadrupole-time-of-flight (Q-TOF) or quadrupole-orbitrap instrument, such as in parallel reaction monitoring (PRM).

In some embodiments, the method is not limited by any lower-limit of quantification (LLOQ) and/or upper-limit of quantification (ULOQ). In some embodiments, the LLOQ is 0.167 ng/mL/hr and the upper limit of quantification (ULOQ) is 66.667 ng/mL/hr. In some embodiments, the calibration curve contains the AngI peptide at an LLOQ of 0.25 ng/mL and a ULOQ of 100 ng/mL Methods of Generating Reports In at least one aspect, the invention provides methods for generating a report for diagnosing a disease or condition associated with reduced activity of plasma renin in a subject. One example of such a disease or condition is hypertension. Another example of such a disease or condition is aldosteronism. Such a method may include the steps of incubating the sample to generate AngI and then optionally adding an SIL-AngI peptide as an internal standard prior to termination of the reaction and then generating an AngI peptide cleavage product and the optional SIL-AngI cleavage product. The method may further include optionally chromatographically separating the AngI cleavage product and the optional SIL-AngI cleavage product from other components of the sample using liquid chromatograph ionizing the AngI cleavage product and the optional SIL-AngI cleavage product to generate multiply charged ions that are analyzed by mass spectrometry to determine the amount of AngI cleavage product and the optional SIL-AngI cleavage product in the sample. In an embodiment where the SIL-AngI internal standard is used, a ratio of the determined amounts of the AngI cleavage product and the SIL-AngI product is indicative of the amount of activity of plasma renin activity in the sample. The methods may further comprise generating a report that recites the amount of activity of plasma renin activity and/or AngI in the sample.

Based on the information on the amount of activity of plasma renin in the sample, one could assess whether a subject has an abnormally low amount of such activity. Such information can be useful for diagnosing one or more diseases or disorders that may be associated with aberrant levels of plasma renin activity in a subject. The features and embodiments of all steps except the steps of generating the report are described immediately above. As noted above, the method can employ more than one column, e.g., two or more columns in parallel connected inline to the same mass spectrometer.

In some embodiments, a plasma renin activity measurement may be used to determine the presence and/or amount of a plasma renin inhibitor in the sample. By mixing at a known ratio a sample with known low activity with a sample with known normal activity, the activity of the resulting mixed sample may be measured. Based on the known ratio of the mixture and known activity of the individual samples, one can compare the measured activity in the mixture to the expected activity in the mixture, whereby a measured activity lower than the expected activity is indicative of the presence and amount of inhibitor in the low activity sample.

Systems

In another aspect, the invention provides systems for determining the presence or amount of plasma renin activity in a sample. Such systems can include various embodiments and sub-embodiments analogous to those described above for methods according to the embodiments of the present invention. These systems include various stations and/or components. As used herein, the term "station" is broadly defined and includes any suitable apparatus or collections of apparatuses (e.g., components) suitable for carrying out the recited method. The stations need not be integrally connected or situated with respect to each other in any particular way. The invention includes any suitable arrangements of the stations with respect to each other. For example, the stations need not even be in the same room. But in some embodiments, the stations are connected to each other in an integral unit.

Figure 2:
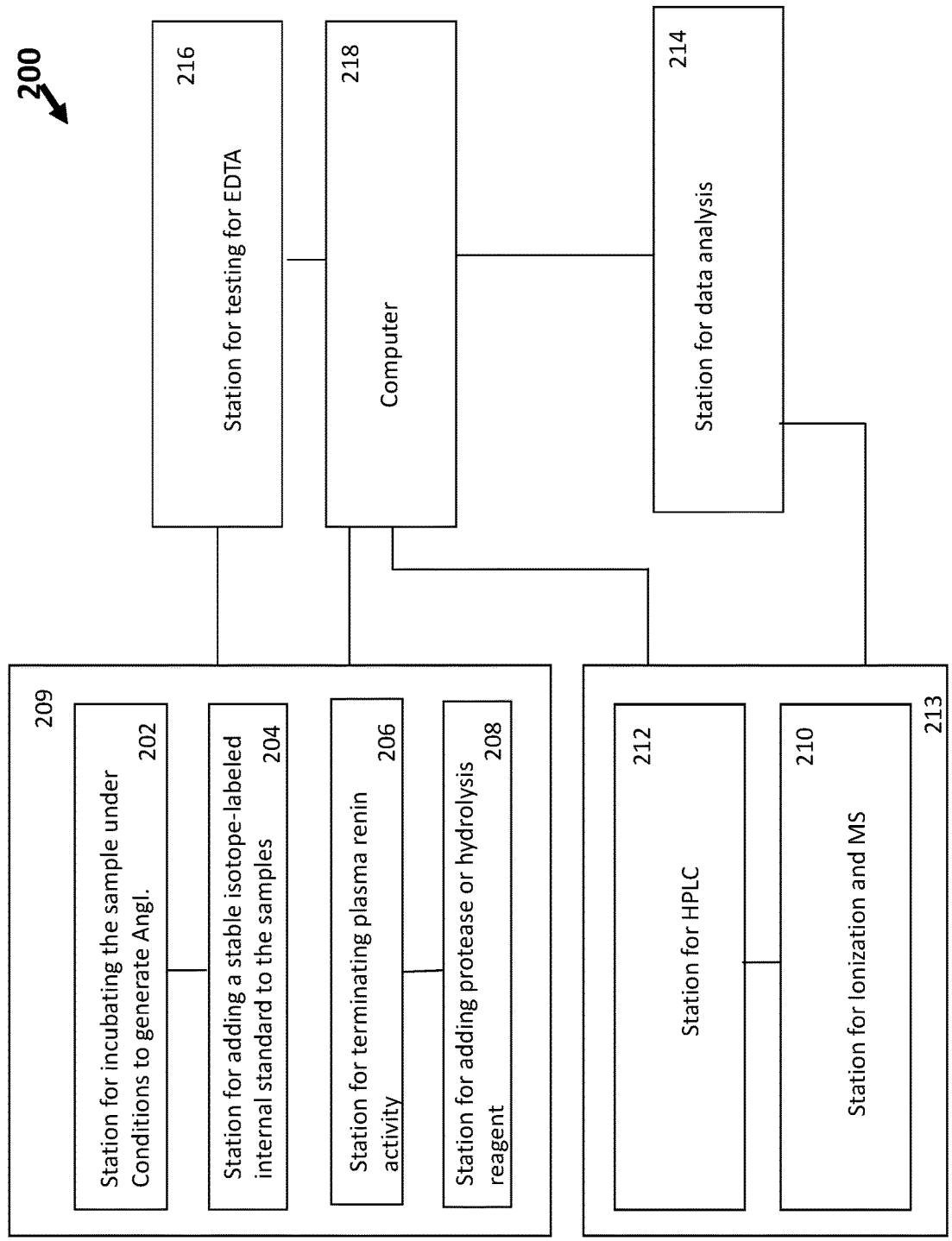
FIG. 2 is a schematic of an embodiment of a system of the invention.

For example, and referring now to FIG. 2, a system (200) may comprises a station (202) for incubating the sample under conditions to generate AngI. Optionally, the system may further comprise a station (204) for adding a stable isotope-labeled peptide SIL-AngI as an internal standard to the sample. The system may further comprise a station (206) to add an agent (e.g., a solvent such as methanol) to terminate the activity of plasma renin. This station may include components to evaporate the solvent and reconstitute the sample in a protease digestion buffer. The system may include a station (208) for adding a protease (e.g., trypsin) to generate an AngI cleavage product and an optional SIL-AngI cleavage product. In some embodiments, at least some of the station for incubating the sample, adding the internal standard, termination plasma renin activity, and addition a protease may be combined as a single station (209)

The system may further comprise allowing a station (210) for multiply charging (i.e., ionizing) and analyzing the AngI cleavage product and the optional SIL-AngI cleavage product by mass spectrometry to determine the amount of the AngI cleavage product and the optional SIL-AngI cleavage product in the sample, wherein the amount of the AngI cleavage product is indicative of the activity of plasma renin in the sample. Optionally, the system may also comprise a station (212) for chromatographically separating the AngI cleavage product and the optional SIL-AngI cleavage product using liquid chromatography or other separation methods (e.g., capillary electrophoresis). In an embodiment, the station for liquid chromatography and mass spectrometry may comprise a single station (213).

The system may further comprise a station or component for data analysis (214). Also, the system may also include a station for testing the sample for the presence of EDTA (216). The system, or parts of the system may be controlled by a computer (218).

The methods and systems according to the embodiments of the present invention possess various advantages. In one embodiment, the method uses a 90 minute incubation to generate AngI compared to other embodiments which use 3-18 hr incubations, providing a faster method. In another embodiment, the method uses a colorimetric reagent and buffer to differentiate EDTA-Plasma from other specimen types, thus ensuring the correct sample type is used. In another embodiment, hydrolysis can be used to alter the selectivity and/or sensitivity of the method.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Non-Limiting Embodiments

Non-limiting embodiments include:

1. A method for determining the amount of AngI in a sample, the method comprising:
(a) Incubating the sample under conditions suitable to allow plasma renin to generate AngI peptide having the sequence NH2-DRVYIHPFHL-COOH (SEQ ID NO: 1) from angiotensinogen present in the sample;
(b) adding a protease or chemical hydrolyzing agent;
(c) incubating the sample under conditions to allow the protease or chemical hydrolyzing agent to hydrolyze the AngI to generate a defined AngI cleavage product;
(d) ionizing the AngI cleavage product to produce one or more ions detectable by mass spectrometry; and
(e) detecting the AngI cleavage product ions by mass spectrometry.

2. The method of paragraph 1, further comprising adding a stable isotope-labeled AngI peptide (SIL-AngI) to the sample as an internal standard.

3. The method of paragraph 2, wherein the SIL-AngI is a peptide NH2-DRVˆYIHPˆFˆHL-COOH (SEQ ID NO: 3) wherein ˆ indicates an amino acid labeled with a heavy isotope.

4. The method of paragraph 3, wherein Vˆ is $(13C)5H11(15N)O2$, having a mass shift of +6; Pˆ is $(13C)5H9(15N)O2$, having a mass shift of +6; and Fˆ is $(13C)9H11(15N)O2$, having a mass shift of +6.

5. The method of paragraph 2, wherein the SIL-AngI is generated from the peptide NH2-DRVYIHPFHL-COOH (SEQ ID NO: 1) using other combinations of amino acids labeled with a heavy isotope.

6. The method of paragraph 2, wherein the SIL-AngI peptide is added before or after plasma renin mediated generation of AngI, but prior to the step of adding a protease.

7. The method of paragraph 2, wherein the amount of AngI cleavage product is directly proportional to the amount of an SIL-AngI cleavage product generated by the protease.

8. The method of paragraph 1, further comprising generating a plurality of calibration standards comprising known amounts of AngI in a suitable matrix, wherein the reference standards are AngI of SEQ ID NO: 1 that goes through the same steps as the sample AngI.

9. The method of paragraph 8, wherein the amount of AngI in the sample is quantified by comparing the amount of AngI in the sample to the amount of AngI in at least one of the plurality of calibration standards.

10. The method of paragraph 9, wherein the calibration standards comprise AngI ranging from 0.25 to 100 ng/mL.

11. The method of paragraph 1, wherein the protease is a serine protease.

12. The method of paragraph 1, wherein the protease is trypsin.

13. The method of paragraph 1, wherein the chemical hydrolysis agent is formic acid, acetic acid, hydrochloric acid, or any other agent capable of hydrolyzing AngI.

14. The method of paragraph 1, wherein protease cleavage generates an AngI cleavage product having the sequence NH2-VYIHPFHL-COOH (SEQ ID NO: 2).

15. The method of paragraph 3, herein the protease generates a SIL-AngI cleavage product having the sequence NH2-VˆYIHPˆFˆHL-COOH (SEQ ID NO: 4).

16. The method of paragraph 1, wherein the AngI ions are selected from the group consisting of ions having a mass/charge ratio of $513.3\pm2$, $269.2\pm2$, $392.7\pm2$, $257.1\pm2$.

17. The method of paragraph 2, wherein the SIL-AngI ions are selected from the group consisting of ions having a mass/charge ratio of $524.3\pm2$, $779.5\pm269$ $0.2\pm2$.

18. The method of paragraph 1, further comprising terminating plasma renin activity prior to the step of protease digestion.

19. The method of paragraph 18, wherein methanol is added to the sample to terminate plasma renin activity.

20. The method of paragraph 19, further comprising evaporating the methanol and then reconstituting the sample in a buffer prior to the step of protease digestion.

21. The method of paragraph 1, wherein the AngI cleavage product, and the optional SIL-AngI cleavage, product are subjected to liquid chromatography prior to mass spectrometry.

22. The method of paragraph 1, wherein the ionization is positive electrospray ionization with selected reaction monitoring (SRM).

23. The method of paragraph 1, wherein the sample is a biological fluid obtained from a patient.

24. The method of paragraph 23, wherein the biological fluid is plasma.

25. The method of paragraph 24, wherein the biological fluid comprises ethylenediaminetetraacetic acid (EDTA) as an anticoagulant.

26. The method of paragraph 1, further comprising prior to the incubation step to generate AngI, removing an aliquot from the sample and testing for the presence of EDTA.

27. The method of paragraph 26, wherein the test for the presence of EDTA comprises addition of a colorimetric agent, o-cresolphthalein complexone, to react with calcium ions in the sample, such that samples comprising EDTA remain substantially unchanged in color, whereas samples that do not have EDTA turn color due to reaction of calcium with the colorimetric agent.

28. A method of measuring plasma renin activity (PRA) according to any of the preceding paragraphs wherein the level of PRA is calculated based on the amount of AngI peptide in the sample.

29. The method of paragraph 28, wherein the plasma renin activity is defined by the amount of AngI generated per unit time.

30. The method of paragraph 28, wherein the plasma renin activity is expressed as ng/mL/hr.

31. The method of paragraph 28, wherein the plasma renin activity has an analytically measurable range (AMR) ranging from about 0.167-66.667 ng/mL/hr.

32. The method of paragraph 28, wherein the lower limit of quantification (LLOQ) is 0.167 ng/mL/hr and the upper limit of quantification (ULOQ) is 66.667 ng/mL/hr.

33. A system for determining the level of AngI and/or the activity of plasma renin in a sample, the system comprising:
 (a) a station for incubating the sample under conditions to generate AngI from angiotensinogen;
 (b) optionally, a station for adding SIL-AngI to the AngI peptide;
 (c) optionally, a station for termination of plasma renin mediated generation of AngI;
 (d) a station for digesting or chemically hydrolyzing the AngI and the optionally added SIL-AngI to generate cleavage products of each of the AngI and the optional SIL-AngI;
 (e) a station for ionizing the AngI and the optional SIL-AngI cleavage products to generate a multiply charged gas-phase ions of the AngI cleavage product and the optional SIL-AngI cleavage product; and
 (f) a station for analyzing the multiply charged gas phase ion by mass spectrometry to determine the presence and/or amount of the AngI cleavage product and the optional SIL-AngI cleavage product in the sample, wherein the amount of the cleavage products is indicative of the activity of plasma renin in the sample.

34. The system of paragraph 33, further comprising a station for testing the sample for the presence of EDTA.

35. The system of paragraph 33, further comprising a station for chromatographically separating the cleavage product using liquid chromatography.

EXAMPLES

Example 1—Assay Reagents and Procedures

Plasma Renin Activity (PRA) is determined by LC-MS/MS using external calibration curves. The assay includes a 1.5 hr bioassay to generate Angiotensin 1, methanol precipitation, evaporation and reconstitution, and tryptic digestion to produce a proteolytic peptide specific to AngI. A stable isotope-labeled peptide (SIL-AngI) is added before methanol precipitation, such that SIL-AngI also undergoes precipitation, evaporation, reconstitution, and digestion. Following digestion of the signature and internal-standard peptides, samples are injected onto a SCIEX 5500 Triple Quadrupole LC-MS/MS system for detection by positive electrospray ionization with selected reaction monitoring (SRM). The amount of AngI in each sample is back-calculated from the corresponding calibration curve generated by spiking a surrogate matrix with AngI reference standard material from 0.25 to 100 ng/mL. PRA is defined by the amount of AngI per unit time, expressed as ng/mL/hr, making the analytically measurable range (AMR) for this assay 0.167-66.667 ng/mL/hr.

Specimens

A recommended sample is 1 mL of plasma dispensed in EDTA. Collection tubes are generally filled to completion to ensure a proper blood to anticoagulant ratio and mixed immediately by gentle inversion to ensure adequate mixing. Plasma should be separated from cells within 4 hours of venipuncture and frozen until tested. As described below, the presence of sufficient EDTA in a sample may be tested using a colorimetric agent (e.g., o-cresolphthalein complexone) that upon chelation of calcium ions will turn purple. If the sample contains sufficient EDTA to complex the calcium ions in the sample, the sample will not change color. If the sample does not include sufficient EDTA to complex the calcium ions in the sample, the sample will change color.

Colorimetric Buffer

Measure 19 mL of 2-amino-2-methyl-1-propanol reagent and add to 75 mL of distilled or deionized water. Adjust the pH to 10.7 using 3.0-3.4 mL 6N hydrochloric acid. QS to 125 mL using deionized or distilled water. Store in an amber bottle. Store at room temperature (15-30° C.) for 3 weeks.

Colorimetric Reagent

Add 15 mL of 6N hydrochloric acid to 12.5 mL deionized or distilled water. Transfer 25 mg o-cresolphthalein complexone to the solution. Rinse the weighing vessel thoroughly to remove all of the powder using the Colorimetric Buffer already prepared. QS to 250 mL using distilled or deionized water. Store at room temperature (15-30° C.) for up to 1 month.

Liquid Chromatography

For HPLC, 5% DMSO, 0.1% Formic Acid in water is used as the A mobile phase and 5% DMSO, 0.1% Formic Acid in acetonitrile is used as the B mobile phase.

Plasma Renin and Protease Digestion

PMSF (100 mM) is prepared in methanol; PMSF is added to inhibit proteases other than plasma renin in the initial incubation to generate AngI. Protease digestion, to generate AngI and SIL-AngI cleavage products, is performed using trypsin (40 μg/mL Trypsin in 50 mM Acetic Acid) in 300 mM Tris-Cl, pH 8.0; 0.001% (w/v) Zwittergent 3-16.

Preparation of Working Internal Standard Solution (SIL-AngI)

The cleavable, labeled peptide (SIL-AngI) is assigned by amino acid analysis (e.g., 100 per vial). One vial is reconstituted using 1 mL of Carrier Matrix (1% (w/v) BSA in 100 mM Tris-Acetate, pH 6) by vortexing for 30 seconds and then incubating at room temperature for ≥15 minutes to produce a 0.1 mg/mL stock solution. The working internal standard solution is created by combining 0.75 mL of the stock internal standard solution with 50 mL of carrier matrix in a clean 200 mL volumetric flask. QS to 200 mL using carrier matrix. Cover, mix well, immediately aliquot for storage. Store at room temperature for up to 2 hours and discard any residual after use.

```
                                              (SEQ ID NO: 3)
Sequence: NH2-DRV^YIHP^F^HL-COOH
Label:
  V^ = (13C)5H11(15N)O2 [Mass Shift +6]
  P^ = (13C)5H9(15N)O2 [Mass Shift +6]
  F^ = (13C)9H11(15N)O2 [Mass Shift +6]
```

Assay Procedure
1. Thaw samples and calibrators using a circulating water bath at 25° C. Trypsin solution should be thawed just before initiating step 3, such that when it is used in step 13 is within 1 hour of removal from the freezer.
2. Pre-heat water bath to 37° C. for subsequent steps.
3. Pipette 200 μL of blanks, standards, controls, and samples to a 2-mL, 96 deep well plate, Plate A. Then, pipette 20 μL of blanks, standards, controls, and samples to 96-well microtiter plate (Plate C) for colorimetric screening.
4. Pipette 100 μL of 100 mM PMSF in MeOH to 10 mL of Generation Buffer (275 mM Maleic Acid, pH 1.8). Vortex 5 seconds and immediately transfer 20 μL of Generation Buffer to each well of Plate A using a 12-channel pipette.
5. Centrifuge Plate A briefly, seal using a Microtiter Plate Sealer, vortex for 30 seconds at 1500 rpm, and incubate in the water bath at 37° C. for 1.5 hr.
6. Transfer 50 μL of colorimetric buffer and reagent to Plate C. Samples that appear purple are to be marked on the coversheet as NOT EDTA-Plasma.
7. After generation, centrifuge Plate A briefly, then add 50 μL of working internal standard solution (300 ng/mL SIL-AngI in Carrier Matrix) to each well except for the double blank, which receives 50 μL of Carrier Matrix.
8. Centrifuge Plate A for 10 seconds at 3500 rpm, seal using a Microtiter Plate Sealer, and vortex for 1 min at 25° C. and 1500 rpm using a ThermoMixer.
9. Add 600 μL of methanol to each well of Plate A, seal the plate using a foil seal and vortex 5 min at 1500 rpm.
10. Centrifuge Plate A for 10 min at 3500 rpm.
11. Transfer 200 μL of supernatant from Plate A to a new 2-mL, 96 deep-well plate (Plate B).
12. Evaporate the contents of Plate B to dryness using a TurboVap (Flow: 40Fh, Temp: 50° C.)
13. Pipette 150 μL of Digestion Buffer into Plate B.
14. Pipette 50 μL of Trypsin Solution to each well of Plate B and centrifuge the plate for 10 seconds at 3500 rpm.
15. Seal Plate B using a Microtiter Plate Sealer, incubate for 30 minutes at 25° C. and 1500 rpm on the ThermoMixer.
16. Pipette 20 μL of Quench Solution to each well of Plate B.
17. Vortex Plate B for 5 min @ 1500 rpm and centrifuge for 10 seconds at 3500 rpm.

Precursor/Fragment Ions

For the AngI cleavage peptide (SEQ ID NO: 2) (AngIdesDR) the transitions are selected from the group consisting of: 650.3±2, 763.4±2, 513.3±2, 269.2±2, 392.7±2, 257.1±2 For the SIL-AngI cleavage peptide (SEQ ID NO: 4) (IS) the transitions are selected from the group consisting of: 524.3±2, 779.5±2, and 269.2±2.

Example 2—Validation of the Assay

The LC-MS/MS method to measure PRA for validation of quantitative methods intended for use in clinical diagnostic testing and routine clinical trials was validated as summarized below. The validation included evaluations of matrix effects, sensitivity, selectivity, stability, inaccuracy, imprecision, linearity, inter-assay comparisons, reference-interval verification, and automation.

Specificity of the assay in calibrator matrix (Carrier Matrix: 1% (v/v) BSA, 100 mM Tris-Acetate, pH 6.0) was assessed by evaluating the interference among the matrices for AngI and SIL-AngI using both (6- and 8-point) calibration series. No interference was observed in calibrator matrix (Carrier Matrix: 1% (w/v) BSA, 100 mM Tris-Acetate, pH 6.0, Table 2, 81) and the assay specificity for AngI is unaffected by SIL-AngI. Further, carryover following the ULOQ is less than that observed in the LLOQ. These results indicate the assay is specific for the analysis of AngI in calibrator matrix.

Given the specificity of the assay, the accuracy and precision of the calibrators and quality controls was evaluated across intra-assay (20×1) and inter-assay (6×3, 5×5 or 1×20) studies. The results indicated the assay is accurate and precise for the detection of AngI and PRA. For example, recovery at the LLOQ was ≤±±20% bias and ≤20% CV to the nominal concentration and recovery at the ULOQ was ≤±±15% bias and ≤15% CV across all studies. Calibrator reproducibility was shown across 5 separate analytical runs. The relative accuracy of the assay in carrier matrix and EDTA-Plasma was evaluated by performing mixing and spike and recovery studies. Accurate AngI measurements after mixing of a high-level calibrator and EDTA-plasma at 3:1, 1:1, and 1:3 ratios indicated matrix equivalency of 100±5%. Spike and recovery demonstrates the assay recovers AngI at 5, 10, and 50× the LLOQ in three generated EDTA-plasma specimens (Table 11). These results indicate that the assay is accurate in carrier matrix and EDTA-plasma.

The specificity and accuracy of the assay was interrogated in the presence of interferents. Only 20 mg/dL conjugated bilirubin affects the analytical measurement of AngI, whereas 10 mg/dL conjugated bilirubin does not, nor does 20 mg/dL un-conjugated bilirubin, 3000 mg/dL triglycerides, 500 mg/dL hemoglobin, or 12 mg/dL total protein. Additionally, gross hemolysis, icterus, or lipemia did not affect the accuracy of the PRA assay as demonstrated by sample mixing with a normal EDTA-plasma specimen prior to generation; however, matched draws of normal and hemolyzed specimens demonstrated some systematic bias of PRA measurements. This inconsistency is perhaps due to the difference in the degree of hemolysis between experiments as well as the use of exogenous hemolysate in the former experiment, which may not contain other cellular components that are released from red blood cells in a patient-dependent manner that could interfere with PRA measurements. Thus, the assay is accurate in the presence of interferents, except for conjugated bilirubin levels at or above 20 mg/dL and moderate-to-gross hemolysis, which may be rejected.

Assay accuracy was evaluated for samples are diluted before generation (encompassing the biology) or after extraction (including only the analytical measurement). Results demonstrated that it is preferable that specimens are not be diluted before generation using carrier matrix, but may be diluted after extraction using digestion buffer up to 50-fold. These studies indicate that patients yielding PRA values above the ULOQ (66.667 ng/mL/hr) can be diluted into range after extraction using digestion buffer.

PRA assays often split specimens into two samples for the generation reaction: hot (37° C.) and cold (4° C.). In this format, the final PRA measurement consists of subtracting the AngI measurement in the cold sample from the AngI measurement in the hot sample to produce an adjusted AngI measurement that accounts for the endogenous basal AngI in the PRA calculation. To evaluate if the cold sample is required for clinical interpretation of PRA, the hot and adjusted measurements of 106 patients were compared. Passing-Bablok regression yields a slope of 1.000 and a correlation coefficient of 0.998, with a mean bias of 2.032%. These results indicated that only the hot sample is required for the accurate measurement of PRA.

The stability of samples and trypsin was evaluated. First, calibrator, quality control, and specimen stability was interrogated at room temperature, refrigerated, frozen, and through freeze-thaw cycles. The calibrators are stable through two freeze-thaw cycles, and for 14 days at RT, refrigerated, frozen (−20° C.), and 128 days frozen (<−70° C.). The QCs are also stable through two freeze-thaw cycles, but, in contrast to the calibrators, are stable for 4 hours at RT. Similarly to the calibrators, though, the QCs are stable for 14 days refrigerated or frozen. Also, the quality controls are stable for 35 days at <−70° C. EDTA-Plasma is stable through three freeze-thaw cycles. In comparison to the QCs, EDTA-Plasma is also stable for four hours at room temperature after thawing, yet in contrast to both the QCs and Calibrators is unstable refrigerated. EDTA-Plasma is stable for 14 days frozen (−20° C.). Finally, the stability of working trypsin solution (40 μg/mL in 50 mM Acetic Acid) and stock trypsin solution (32 mg/mL in 50 mM Acetic Acid) was evaluated and observed to be stable frozen for 63 days (<−10° C.) and 244 days (<−70° C.), respectively.

Given the instability of EDTA-Plasma at room temperature, a time-to-freeze stability study of four patients was performed to provide guidance to collection sites for sample handling. Briefly, samples were processed immediately (baseline) or incubated at room temperature (15-30° C.) for 1, 2, or 4 hours prior to freezing. The results indicate EDTA-Plasma is stable when processed and frozen within 4 hours after collection from the patient. Thus, sites of collection should process and freeze EDTA-Plasma samples from patients after collection with minimal interruption.

In-process and post-extraction stability of calibrators, controls, and samples was conducted. Acceptable in-process stability was observed post-generation (on wet ice, 1 hour), post-precipitation (<−10° C., 55 days), and post-digestion (on wet ice, 1 hour). Additionally, acceptable post-extraction stability was observed on the bench-top (15-30° C.) for 4 hours and in the autosampler (10° C.) for 10 days.

To evaluate the harmony among PRA assays, the LC-MS/MS assay was compared to the protocols of Endocrine Sciences (MA), Center for Esoteric Testing (MA, Tables 57, 58), and St. Paul's Hospital (SPH, LC-MS/MS) (G. Van Der Gugten and D. Holmes, "*Quantitation of Plasma Renin Activity in Plasma Using Liquid Chromatography Tandem Mass Spectrometry (LC-MS/MS)*," Clinical Applications of Mass Spectrometry in Biomolecular Analysis, 2016, 1378: 243-253). The LC-MS/MS assay correlated worst to Endocrine Sciences (Slope: 1.123, Mean Bias: 19.6%) and best to SPH (Slope: 1.030, Mean Bias: 1.64%). To verify the SPH reference interval, 142 reference interval specimens were filtered according to Aldosterone, serum Sodium, serum Potassium, History, and blood pressure measurements. Verification of the SPH reference failed (Table 61), due to >10% of samples being below the SPH lower RI limit.

Consequently, de novo reference interval generation was performed. First, 142 specimens were interrogated for normal Aldosterone [0-30 ng/dL], Sodium [3.5-5.2 mmol/L], Potassium [134-144 mmol/L] and history of hypertension. EP Evaluator was used to generate a transformed parametric reference interval of 0.167 ng/mL/hr (fixed at the assay LLOQ) to 5.3804 ng/mL/hr (4.6091-6.2448, 90% CI) and a confidence ratio of 0.16. Given that the PRA assay is evaluated in the context of the Aldosterone-to-Renin Ratio (ARR), the ARR reference interval (ng/dL:ng/mL/hr) was also verified using the 142 filtered specimens. The analytical correlation of the LC-MS/MS aldosterone and PRA assays between the assay described herein and SPH suggests that patient samples interrogated for the ARR at either site would receive similar care.

Agreement between the manual and automated assays was interrogated. Briefly, one manual plate containing QCs and Patient samples was evaluated against two automated plates. Passing-Bablok regression of manual v. automated plate 1 yields a 0.919 slope (0.898-0.938 90% CI), an intercept of −0.0108 (−0.0744-0.0596; 90% CI) with a correlation coefficient of 0.9946. Passing-Bablok regression of the manual v. automated plate 2 yields a 0.948 slope (0.926-0.972 90% CI), an intercept of −0.0406 (−0.1058-0.0104 90% CI) and a correlation coefficient of 0.9921. These data indicate that automation can be used for double-plate batches of this PRA assay.

While the preferred embodiments of the invention have been illustrated and described, it will be appreciated that various changes can be made therein without departing from the spirit and scope of the invention. All printed patents and publications referred to in this application are hereby incorporated herein in their entirety by this reference.

Reference to a Sequence Listing Submitted as a Text File Via EFS-WEB

The official copy of the sequence listing is submitted electronically via EFS-Web as an ASCII formatted sequence listing with a file named Plasmarenin_ST25.txt, created on Nov. 16, 2017, and having a size of 1.51 kilobytes and is filed concurrently with the specification. The sequence listing contained in this ASCII formatted document is part of the specification and is herein incorporated by reference in its entirety.

We claim:

1. A method for determining an amount of AngI in a sample, the method comprising:
   (a) incubating the sample under conditions suitable to allow plasma renin to generate angiotensin I (AngI) of a sequence NH2-DRVYIHPFHL-COOH (SEQ ID NO: 1) from angiotensinogen present in the sample;
   (b) adding a protease;
   (c) incubating the sample under conditions to allow the protease to hydrolyze the AngI to generate a defined AngI cleavage product;
   (d) ionizing the defined AngI cleavage product to produce one or more AngI cleavage product ions detectable by mass spectrometry; and,
   (e) detecting the one or more AngI cleavage product ions by mass spectrometry to determine the amount of AngI in the sample,
   wherein level of plasma renin activity in the sample is calculated based on the amount of AngI in the sample.

2. The method of claim 1, further comprising adding a stable isotope-labeled angiotensin I peptide (SIL-AngI) to the sample as an internal standard.

3. The method of claim 2, wherein the SIL-AngI is a peptide of a sequence NH2-DRV^YIHP^F^HL-COOH (SEQ ID NO: 3), wherein ^ indicates an amino acid labeled with a heavy isotope.

4. The method of claim 3, wherein V^ is (13C)5H11(15N)O2, having a mass shift of +6; P^ is (13C)5H9(15N)O2, having a mass shift of +6; and F^ is (13C)9H11(15N)O2, having a mass shift of +6.

5. The method of claim 2, wherein the SIL-AngI peptide comprises amino acids labeled with a heavy isotope.

6. The method of claim 2, wherein the SIL-AngI peptide is added before or after step (a), but prior to step (b), and the method further comprises generating an SIL-AngI cleavage product by the protease cleavage, and ionizing the SIL-AngI cleavage product to generate SIL-AngI cleavage product ions.

7. The method of claim 6, wherein an amount of AngI cleavage product is directly proportional to an amount of an SIL-AngI cleavage product generated by the protease.

8. The method of claim 1, further comprising generating a plurality of calibration standards comprising known amounts of AngI in a suitable matrix, wherein each of the plurality of the calibration standards comprises AngI of SEQ ID NO: 1 that is subjected to the same steps as the sample AngI.

9. The method of claim 8, wherein the amount of AngI in the sample is quantified by comparing an amount of the one or more AngI cleavage product ions detected in the sample to an amount of one or more AngI cleavage product ions detected in at least one of the plurality of calibration standards.

10. The method of claim 9, wherein the calibration standards comprise AngI ranging from 0.25 to 100 ng/mL.

11. The method of claim 1, wherein the protease is a serine protease.

12. The method of claim 1, wherein the protease is trypsin.

13. The method of claim 1, wherein protease cleavage generates an AngI cleavage product of a sequence NH2-VYIHPFHL-COOH (SEQ ID NO: 2).

14. The method of claim 3, wherein the SIL-AngI peptide is added before or after step (a), but prior to step (b), and wherein the protease cleavage generates a SIL-AngI cleavage product of a sequence NH2-DRV^YIHP^F^HL-COOH (SEQ ID NO: 4).

15. The method of claim 1, wherein the one or more AngI cleavage product ions are selected from the group consisting of ions having a mass/charge ratio of 513.3±2, 269.2±2, 392.7±2, 257.1±2.

16. The method of claim 7, wherein the SIL-AngI cleavage product ions are selected from the group consisting of ions having a mass/charge ratio of 524.3 ±2, 779.5 ±2, and 269.2 ±2.

17. The method of claim 1, further comprising terminating plasma renin activity prior to protease digestion.

18. The method of claim 17, wherein methanol is added to the sample to terminate plasma renin activity.

19. The method of claim 18, further comprising evaporating the methanol and then reconstituting the sample in a buffer prior to the protease digestion.

20. The method of claim 1, wherein the defined AngI cleavage product is subjected to liquid chromatography prior to mass spectrometry.

21. The method of claim 1, wherein the ionizing is performed by positive electrospray ionization with selected reaction monitoring (SRM).

22. The method of claim 1, wherein the sample is a biological fluid obtained from a patient.

23. The method of claim 22, wherein the biological fluid is plasma.

24. The method of claim 23, wherein the biological fluid comprises ethylenediaminetetraacetic acid (EDTA) as an anticoagulant.

25. The method of claim 1, further comprising, prior to step (a), removing an aliquot from the sample and testing the aliquot for presence of EDTA.

26. The method of claim 25, wherein the testing for the presence of EDTA comprises addition of a colorimetric agent, o-cresolphthalein complexone, to react with calcium ions in the sample, such that samples comprising EDTA remain substantially unchanged in color, whereas samples that do not have EDTA turn color due to reaction of calcium with the colorimetric agent.

27. The method of claim 1, wherein the plasma renin activity is defined by the amount of AngI generated per unit time.

28. The method of claim 1, wherein the plasma renin activity is expressed as ng/mL/hr.

29. The method of claim 28, wherein the plasma renin activity has an analytically measurable range (AMR) ranging from about 0.167-66.667 ng/mL/hr.

30. The method of claim 28, wherein a lower limit of quantification (LLOQ) of the plasma renin activity is 0.167 ng/mL/hr and an upper limit of quantification (ULOQ) of the plasma renin activity is 66.667 ng/mL/hr.

31. A method for determining plasma renin activity (PRA) in a sample, the method comprising:
(a) incubating the sample under conditions suitable to allow plasma renin to generate angiotensin I (AngI) of a sequence NH2-DRVYIHPFHL-COOH (SEQ ID NO: 1) from angiotensinogen present in the sample;
(b) before or after step (a), but prior to step (c), adding a stable isotope- labeled angiotensin I peptide (SIL-AngI) to the sample as an internal standard;
(c) adding a protease to the sample;
(d) incubating the sample under conditions to allow the protease to hydrolyze the AngI to generate a defined AngI cleavage product, and to allow the protease to hydrolyze the SIL-AngI peptide to generate an SIL-AngI cleavage product;
(e) ionizing the defined AngI cleavage product to produce one or more AngI cleavage product ions detectable by mass spectrometry, and ionizing the SIL-AngI cleavage product to generate one or more SIL-AngI cleavage product ions detectable by mass spectrometry; and,
(f) detecting the one or more AngI cleavage product ions and the one or more SIL-AngI cleavage product ions to determine an amount of the AngI cleavage product and an amount of the SIL-AngI cleavage product in the sample,
wherein a ratio of the determined amounts of the AngI cleavage product and the internal standard SIL-AngI cleavage product is indicative of an amount of PRA in the sample.

32. The method of claim 31, wherein the SIL-AngI is a peptide of a sequence NH2-DRV^YIHP^F^HL-COOH (SEQ ID NO: 3), wherein ^ indicates an amino acid labeled with a heavy isotope.

33. The method of claim 31, wherein the protease is a serine protease.

34. The method of claim 31, wherein the protease is trypsin.

35. The method of claim 31, wherein protease cleavage generates the defined AngI cleavage product of a sequence NH2-VYIHPFHL-COOH (SEQ ID NO: 2).

* * * * *